United States Patent
Geist et al.

(10) Patent No.: US 11,452,617 B2
(45) Date of Patent: Sep. 27, 2022

(54) DYNAMIC EXPANDING PATHWAY CANNULA

(71) Applicant: Integrity Implants Inc., Palm Beach Gardens, FL (US)

(72) Inventors: Wyatt Drake Geist, Davie, FL (US); John Souza, Monroe, NC (US); Mark Grubb, Cleveland, OH (US)

(73) Assignee: Integrity Implants Inc., Palm Beach Gardens, FL (US)

( * ) Notice: Subject to any disclaimer, the term of this patent is extended or adjusted under 35 U.S.C. 154(b) by 0 days.

(21) Appl. No.: 17/016,080

(22) Filed: Sep. 9, 2020

(65) Prior Publication Data

US 2021/0068981 A1 Mar. 11, 2021

Related U.S. Application Data

(60) Provisional application No. 62/897,750, filed on Sep. 9, 2019.

(51) Int. Cl.
*A61F 2/46* (2006.01)

(52) U.S. Cl.
CPC ..... *A61F 2/4611* (2013.01); *A61F 2002/4627* (2013.01)

(58) Field of Classification Search
CPC ............ A61F 2/4611; A61F 2002/4625; A61F 2002/4627
See application file for complete search history.

(56) References Cited

U.S. PATENT DOCUMENTS

| 8,486,081 | B2* | 7/2013 | Parsons | A61B 17/025 606/99 |
| 8,801,758 | B2* | 8/2014 | Milz | A61F 2/46 606/279 |
| 9,107,650 | B2 | 8/2015 | Bjork et al. | |
| 9,387,088 | B2 | 7/2016 | Roche et al. | |
| 10,143,567 | B2* | 12/2018 | Costabile | A61F 2/447 |
| 2005/0165408 | A1* | 7/2005 | Puno | A61F 2/4611 606/99 |
| 2007/0185375 | A1* | 8/2007 | Stad | A61B 17/025 600/101 |
| 2008/0287957 | A1* | 11/2008 | Hester | A61B 17/025 606/99 |
| 2010/0160983 | A1* | 6/2010 | Runco | A61F 2/4611 606/86 A |

(Continued)

*Primary Examiner* — Kevin T Truong
*Assistant Examiner* — Diana Jones
(74) *Attorney, Agent, or Firm* — McHale & Slavin, P.A.

(57) ABSTRACT

The invention involves a cannula suitable for the implantation of intervertebral implants into the spine area of an animal, particularly humans. The first end of the dynamically expanding cannula includes a rectangular or oval shaped cannula portion formed from a sandwich style assembly. The second end of the dynamically expanding cannula includes a connection assembly for securing the sandwich construction together. Once inserted, a backing assembly can be removed and a flexible expansion member can be displaced by an implant while a slide guides the implant to create a dynamic opening through which the implant travels to the disc space. A lever is supplied as a portion of the expansion assembly for removing the expansion member after insertion of an intervertebral implant.

17 Claims, 22 Drawing Sheets

(56) References Cited

U.S. PATENT DOCUMENTS

| | | | | |
|---|---|---|---|---|
| 2013/0226244 A1* | 8/2013 | Davenport | ............ | A61F 2/4465 606/279 |
| 2014/0330384 A1* | 11/2014 | Puno | .................... | A61F 2/4465 623/17.16 |
| 2014/0343559 A1* | 11/2014 | Flickinger | .............. | A61B 17/88 606/90 |
| 2016/0160983 A1* | 6/2016 | Yanase | .................... | F16H 48/40 475/230 |
| 2017/0202684 A1* | 7/2017 | Padovani | .............. | A61F 2/4684 |

\* cited by examiner

DYNAMIC EXPANDING PATHWAY CANNULA

RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 62/897,750, entitled "DYNAMIC EXPANDING PATHWAY CANNULA", filed on Sep. 9, 2019. The contents of the above application are incorporated herein by reference.

FIELD OF INVENTION

The present invention generally relates to providing a pathway to the internal anatomy of an animal; and more particularly, to a cannula having dynamic pathway expansion for inserting an implant in the spine of an animal such as a human.

BACKGROUND INFORMATION

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints, allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the annulus fibrosus ("annulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae. The annulus of the disc forms the disc perimeter, and is a tough, outer fibrous ring that binds adjacent vertebrae together. The fibrous layers of the annulus include fifteen to twenty overlapping plies, which are inserted into the superior and inferior vertebral bodies at roughly a 40-degree angle in both directions. This causes bi-directional torsional resistance, as about half of the angulated fibers will tighten when the vertebrae rotate in either direction. It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the annulus to buckle in areas where the laminated plies are loosely bonded. As the overlapping laminated plies of the annulus begin to buckle and separate, either circumferential or radial annular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases, it is desired to fuse the adjacent vertebrae together after removal of the disc, sometimes referred to as "intervertebral fusion" or "interbody fusion." In this process, an intervertebral implant and a bone graft are positioned in place of the disc and spondylodesis or spondylosyndesis is used to join two or more vertebrae to eliminate pain caused by abnormal motion, degradation, fractures or deformities of the vertebrae.

Drawbacks to the procedure include infection, blood loss and nerve damage from accessing the disc space. Thus, what is needed is a device for accessing the disc space that provides dynamic pathway expansion for traversal of an implant.

Finally, there are ergonomic needs that a surgical cannula must satisfy in order to achieve acceptance by the end user. The cannula must be easily and quickly assembled using minimal hardware and requiring a minimal number of tools. Further, the cannula should not require excessive strength to assemble or include heavy component parts. Moreover, the cannula must assemble together in such a way so as not to detract from the intended use of the cannula.

Thus, the present invention provides a dynamically expanding pathway cannula which overcomes the disadvantages of prior art cannulas and implant systems. The dynamically expanding pathway cannula of the present invention not only provides for relative ease in assembly and use, it also permits spinal implant implantation without the need to use slide hammers and the like. The present invention also provides a cannula that expands dynamically, thereby minimizing damage and trauma to surrounding tissues and nerves.

SUMMARY OF THE INVENTION

Briefly, the invention involves a cannula suitable for the implantation of intervertebral implants into the spine area of an animal, particularly humans. The first end of the system includes a rectangular or oval shaped cannula formed from a sandwich style assembly. The second end of the system includes a connection assembly for securing the sandwich construction together. Once inserted, the backing assembly can be removed and a flexible expansion member can be displaced by an implant to create a dynamic opening through which the implant travels to the disc space. A lever is supplied as a portion of the expansion assembly for removing the expansion member after insertion of an intervertebral implant.

Accordingly, it is an objective of the present invention to provide a dynamically expanding cannula.

It is a further objective of the present invention to provide a dynamically expanding cannula constructed for placing an intervertebral implant in the disc area of an animal.

It is yet a further objective of the present invention to provide a dynamically expanding cannula that includes a rigid slide member and a cooperating flexible expansion member for insertion of an implant.

It is another objective of the present invention to provide a dynamically expanding cannula having a pulling assembly for removal of the flexible expansion member after insertion of the implant.

Other objectives and advantages of this invention will become apparent from the following description taken in conjunction with the accompanying drawings wherein are set forth, by way of illustration and example, certain embodiments of this invention. The drawings constitute a

BRIEF DESCRIPTION OF THE FIGURES

FIG. 14 is a rear perspective view illustrating an implant bring loaded into the cannula;

DETAILED DESCRIPTION OF THE PREFERRED EMBODIMENTS

Figure 1:
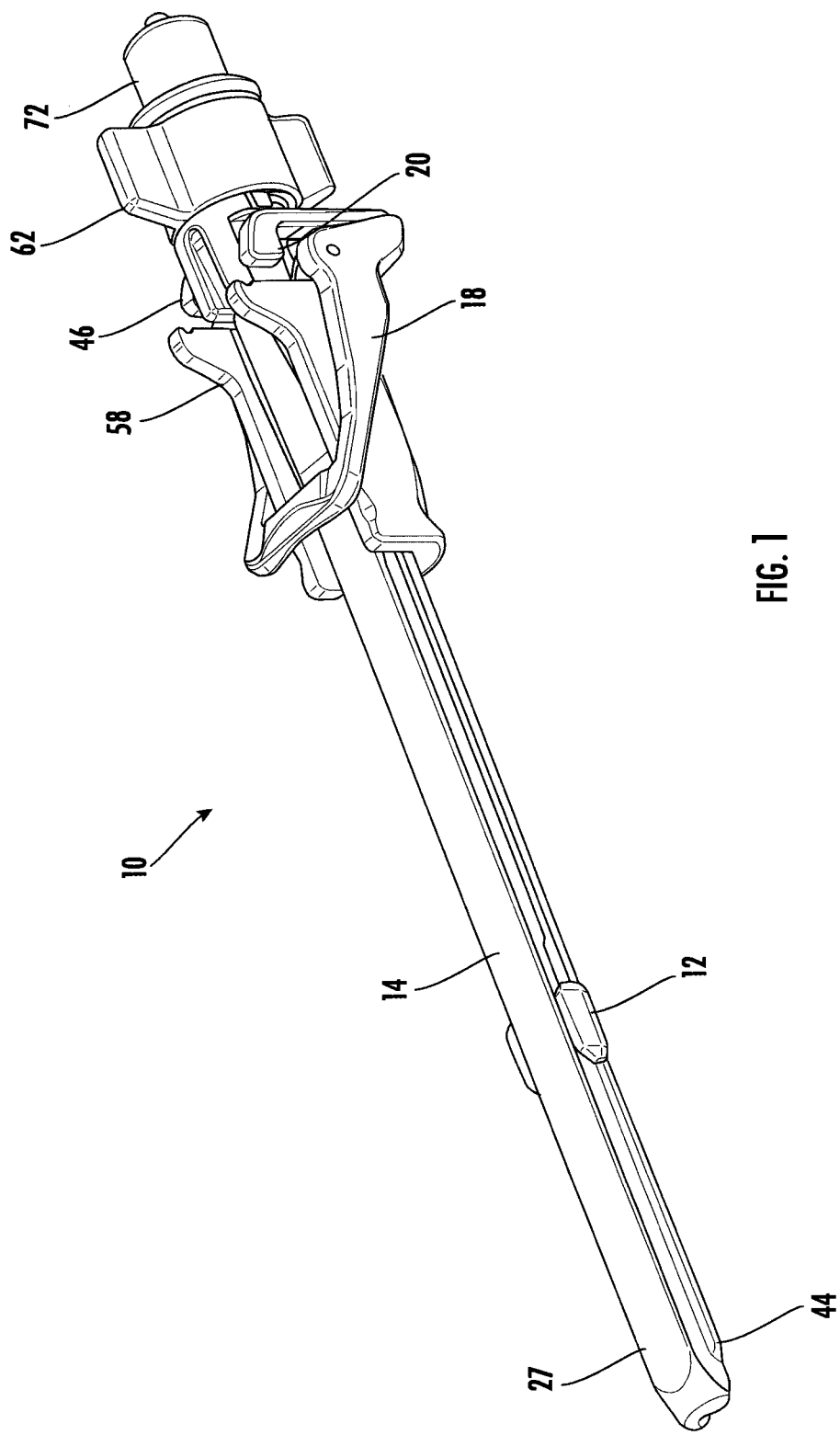
FIG. 1 is a top front left perspective view of one embodiment of the present invention.
Figure 2:
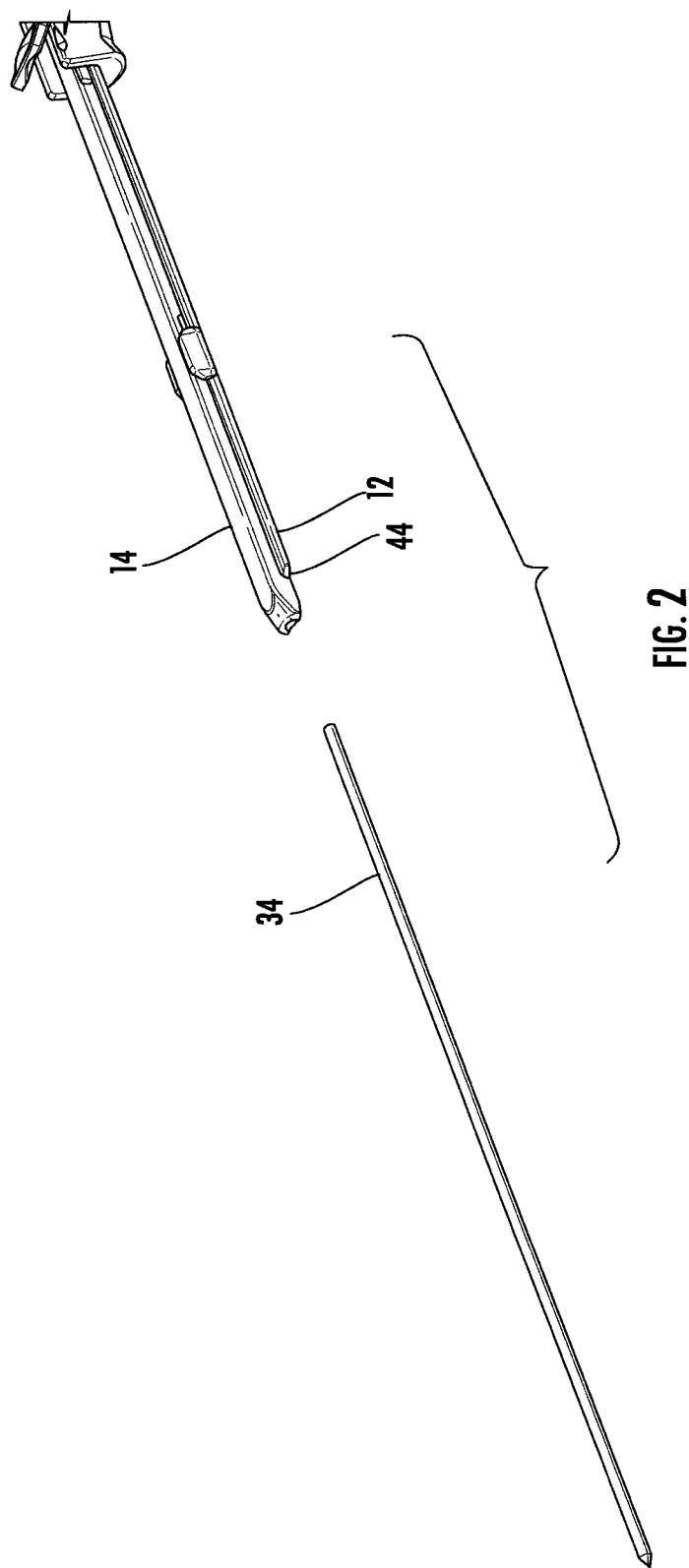
FIG. 2 is a top front left perspective view of the embodiment shown in FIG. 1 illustrating an innermost bore for cooperation with a guide wire.
Figure 3:
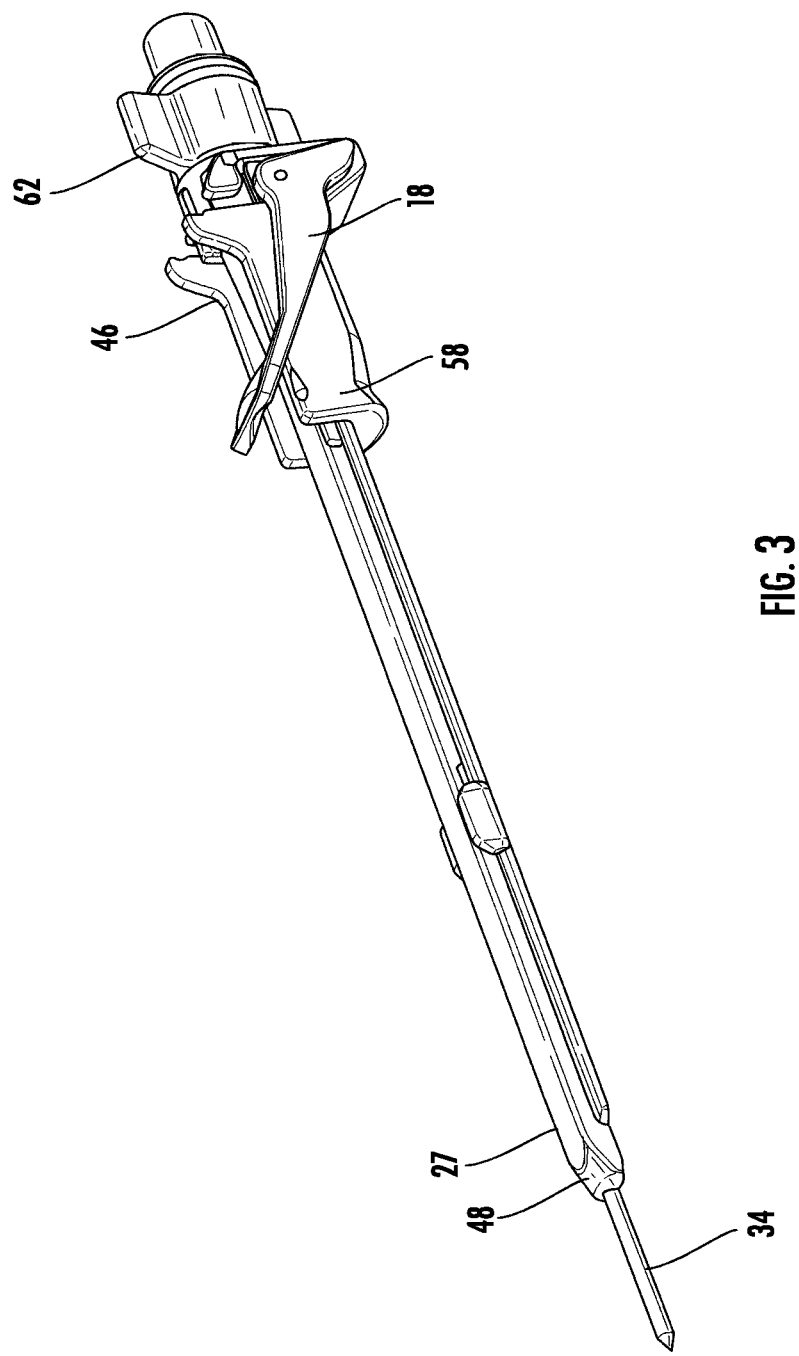
FIG. 3 is a top front left perspective view of the embodiment shown in FIG. 1 illustrating the guide wire inserted in the innermost bore.
Figure 4:
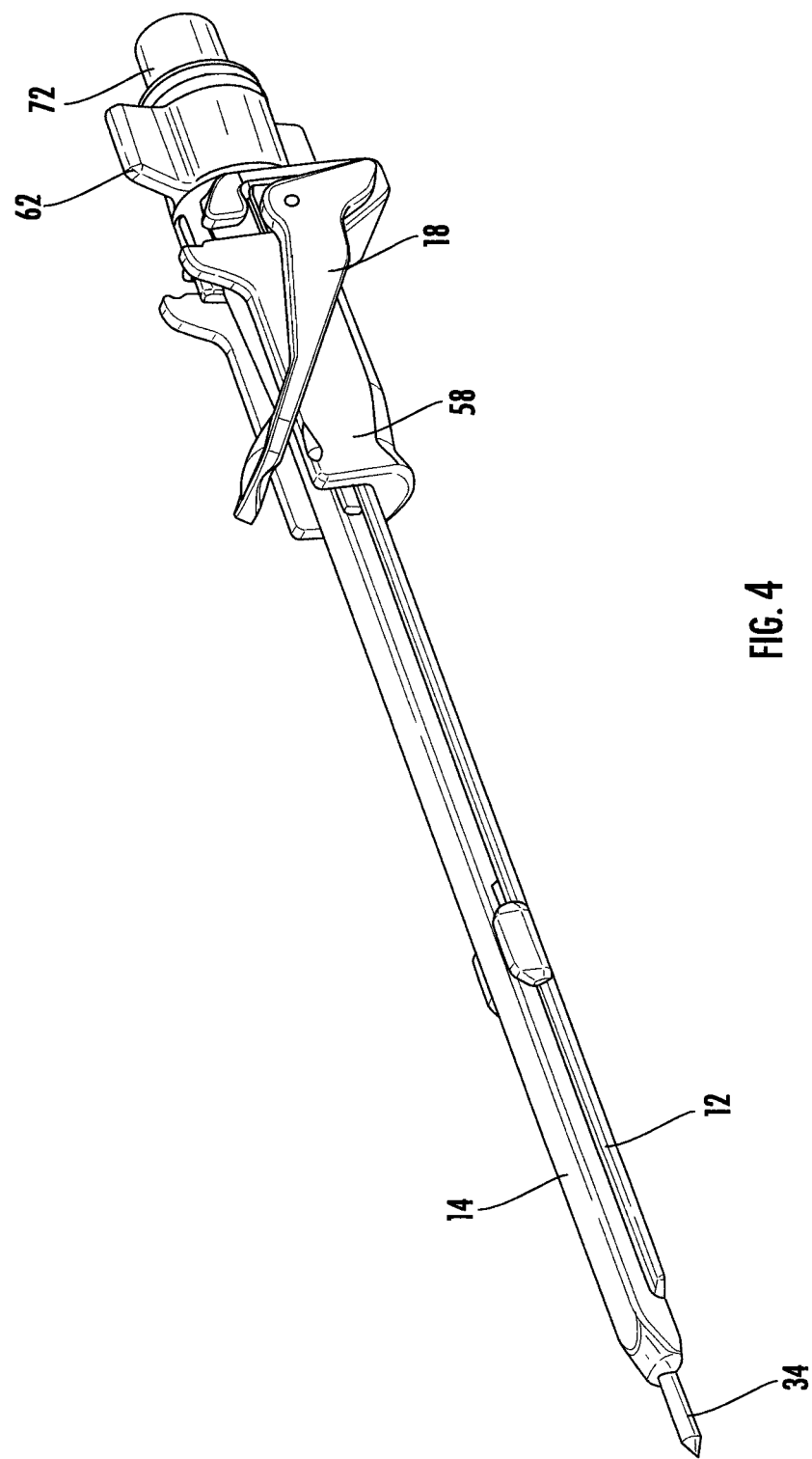
Figure 5:
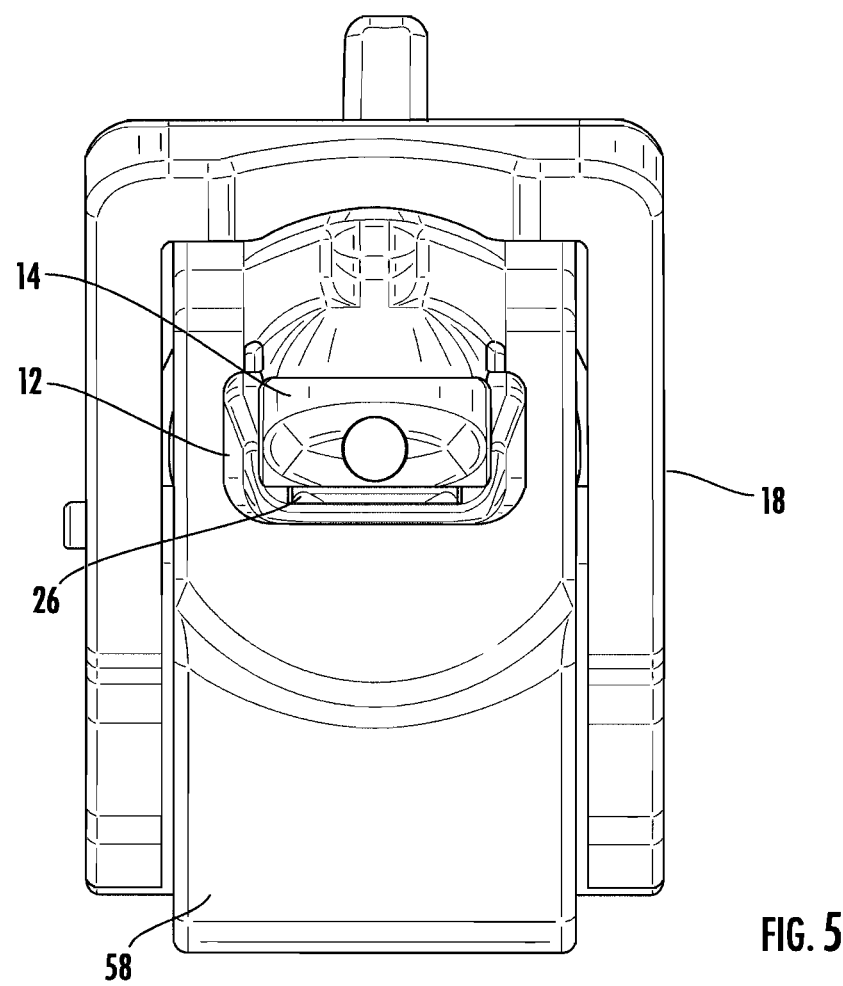
FIG. 5 is a rear end view illustrating assembly of the device.
Figure 6:
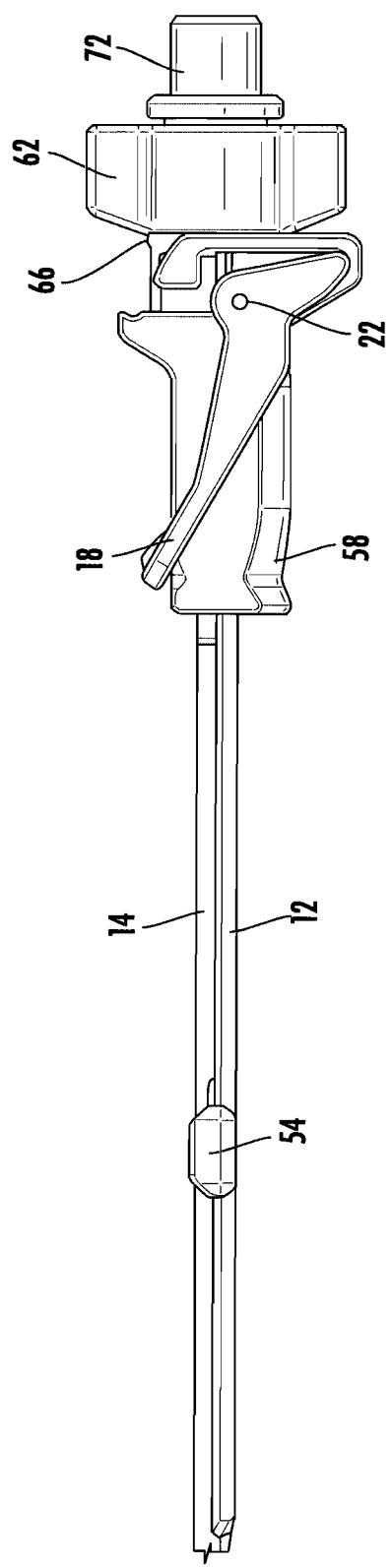
FIG. 6 is a side view of one embodiment of the device.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 7:
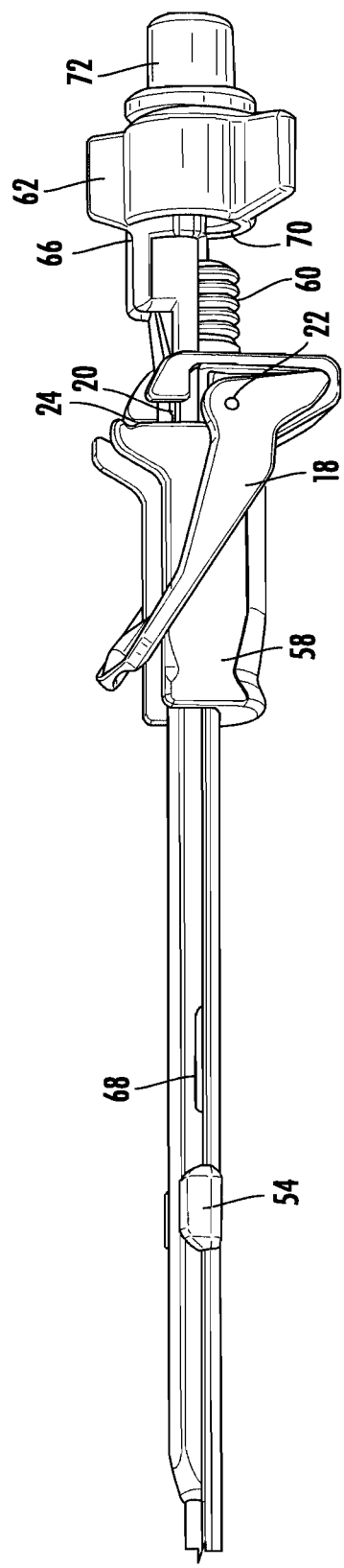
FIG. 7 is a perspective view illustrating removal of the backing assembly.
Figure 8:
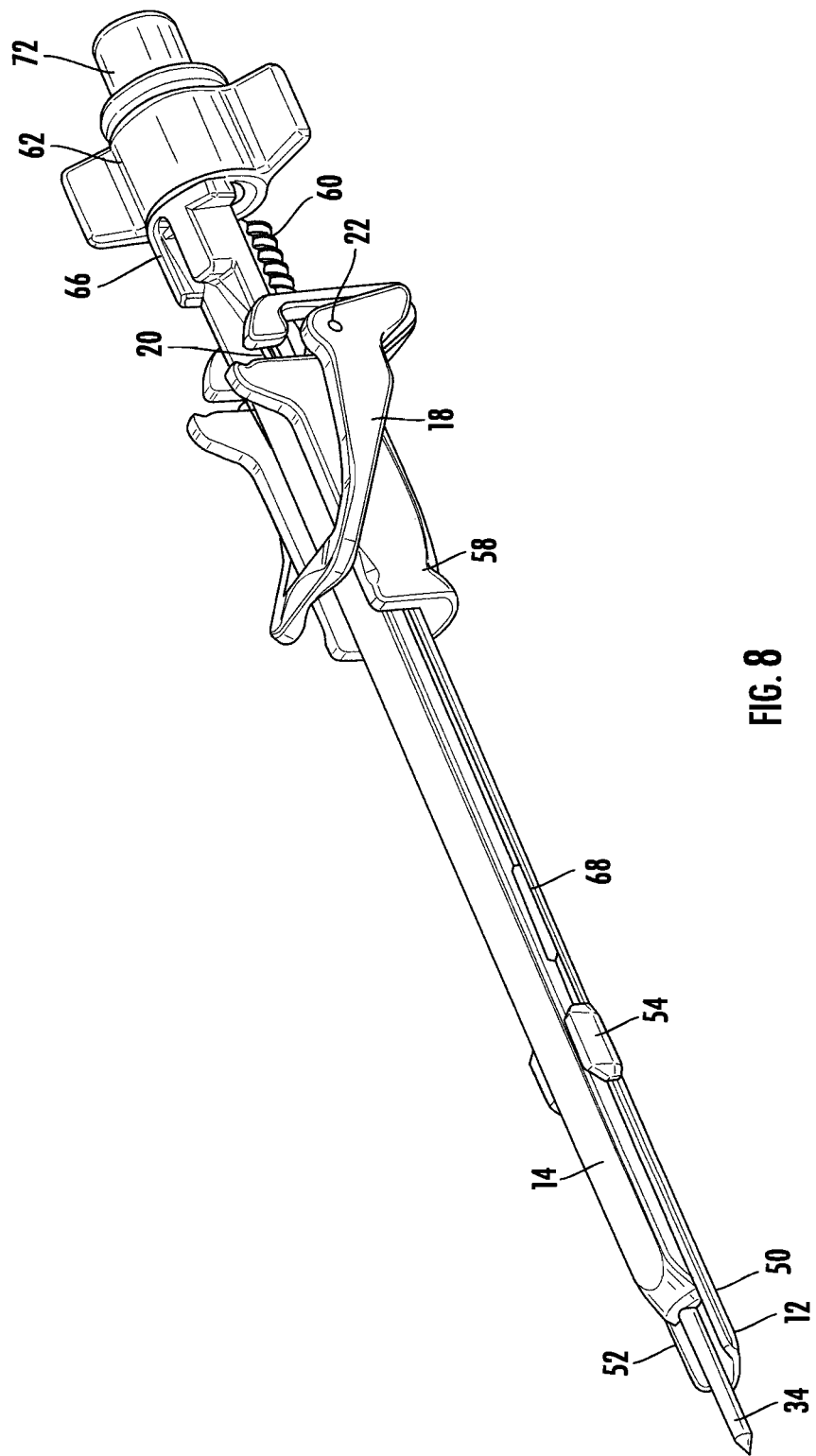
FIG. 8 is a perspective view further illustrating removal of the backing assembly.
Figure 9:
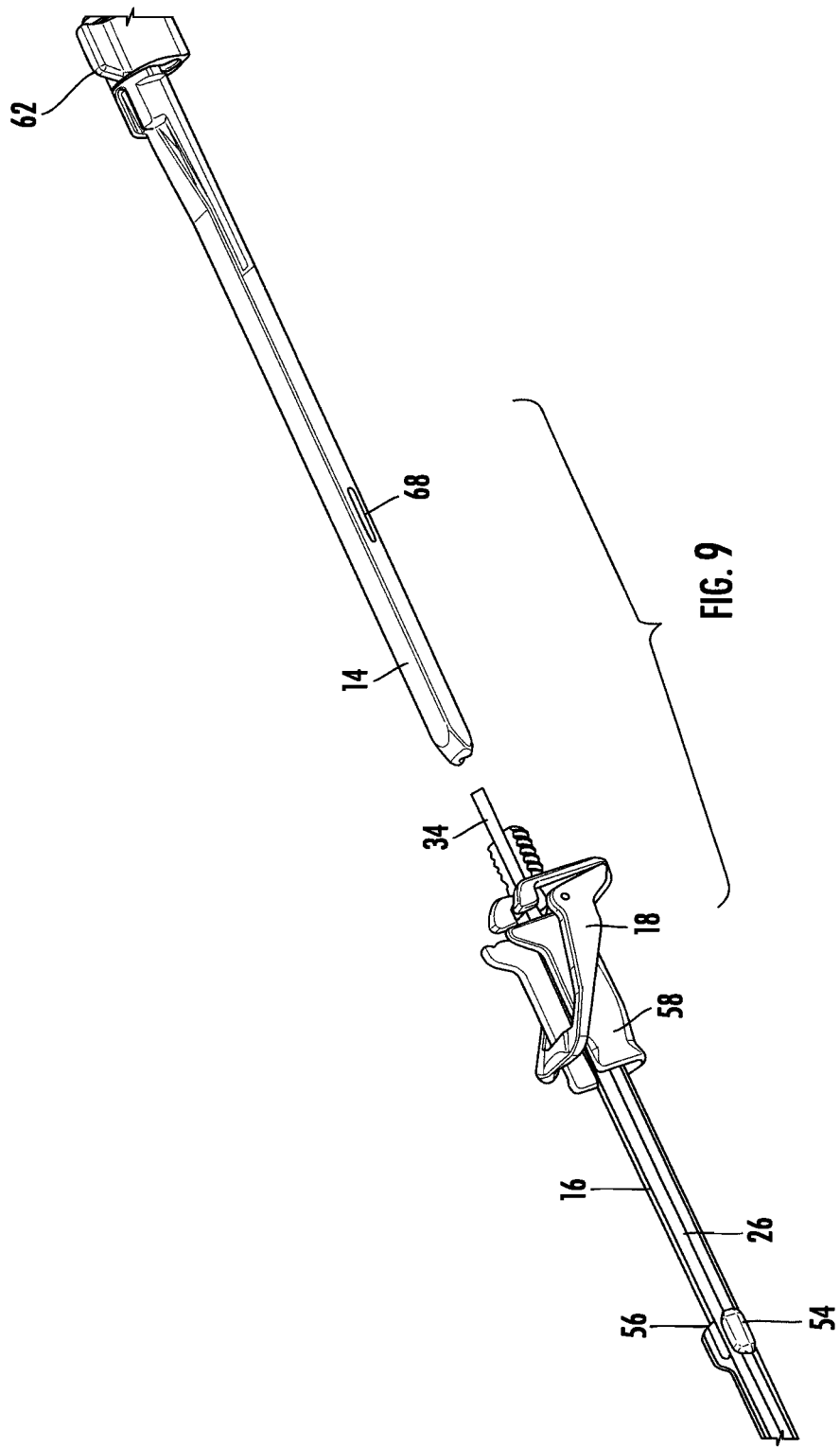
FIG. 9 is a perspective view illustrating full removal the backing assembly.
Figure 10:
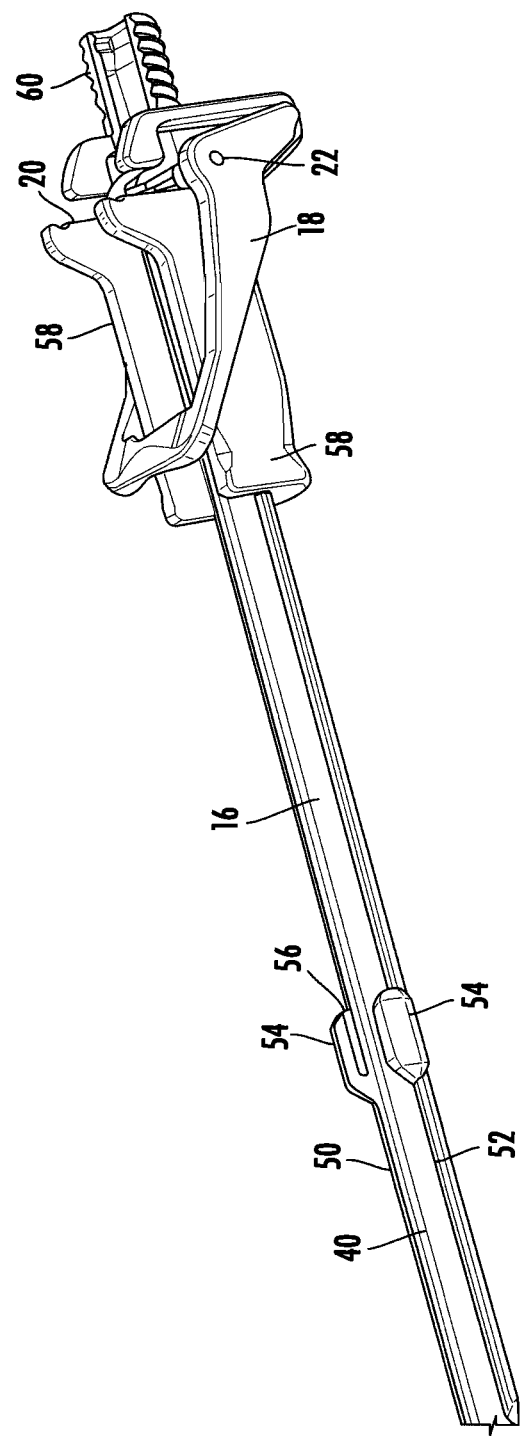
FIG. 10 is a perspective view illustrating the slide assembly and the expansion assembly.
Figure 11:
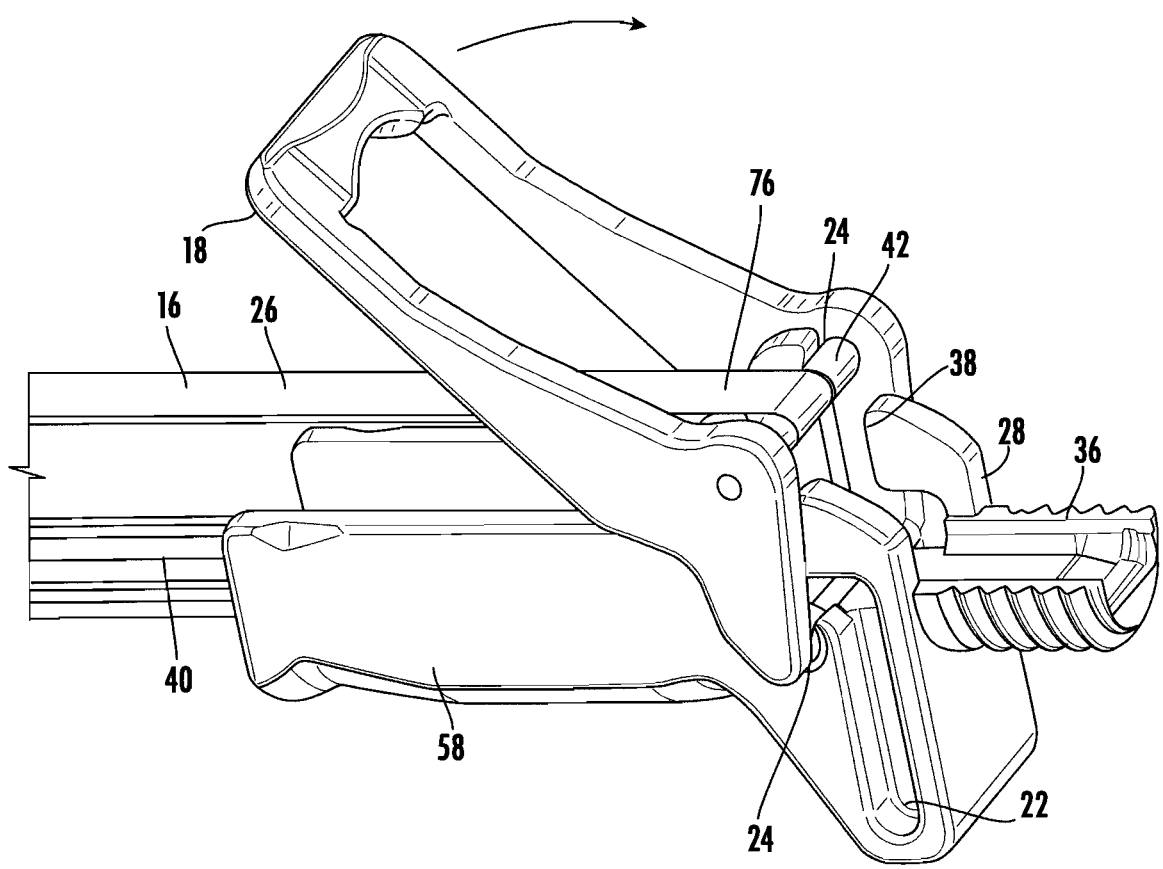
FIG. 11 is a partial perspective view illustrating the puller lever for the expansion member positioned for opening the cannula.
Figure 12:
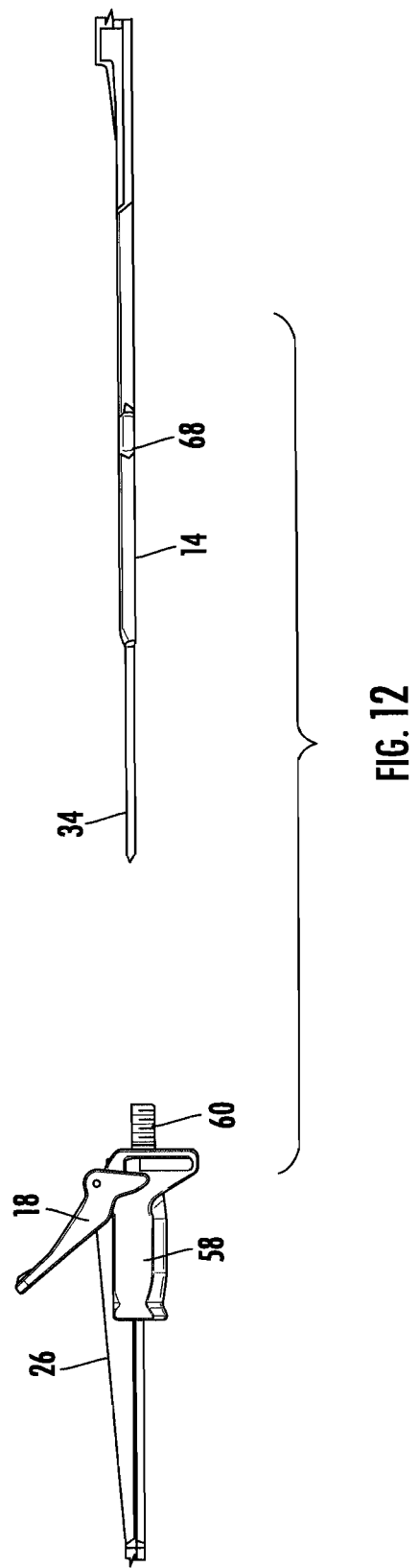
FIG. 12 is a side view illustrating the cannula in an open position for accepting an implant.
Figure 13:
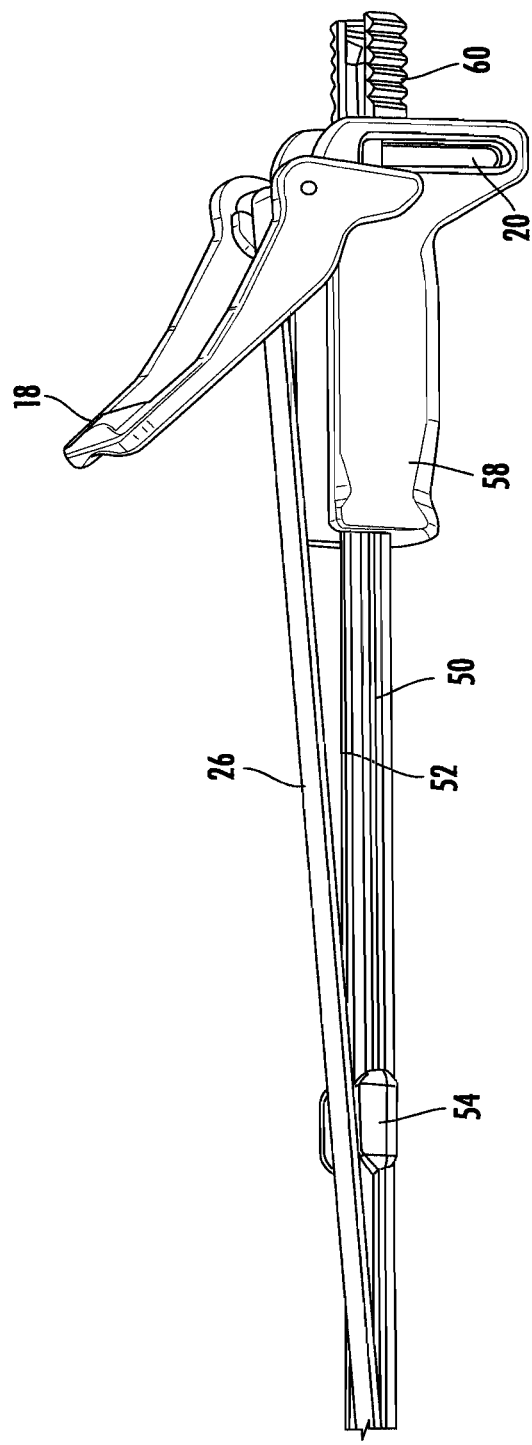
FIG. 13 is a perspective view of the present device illustrated in an open position.
Figure 14:
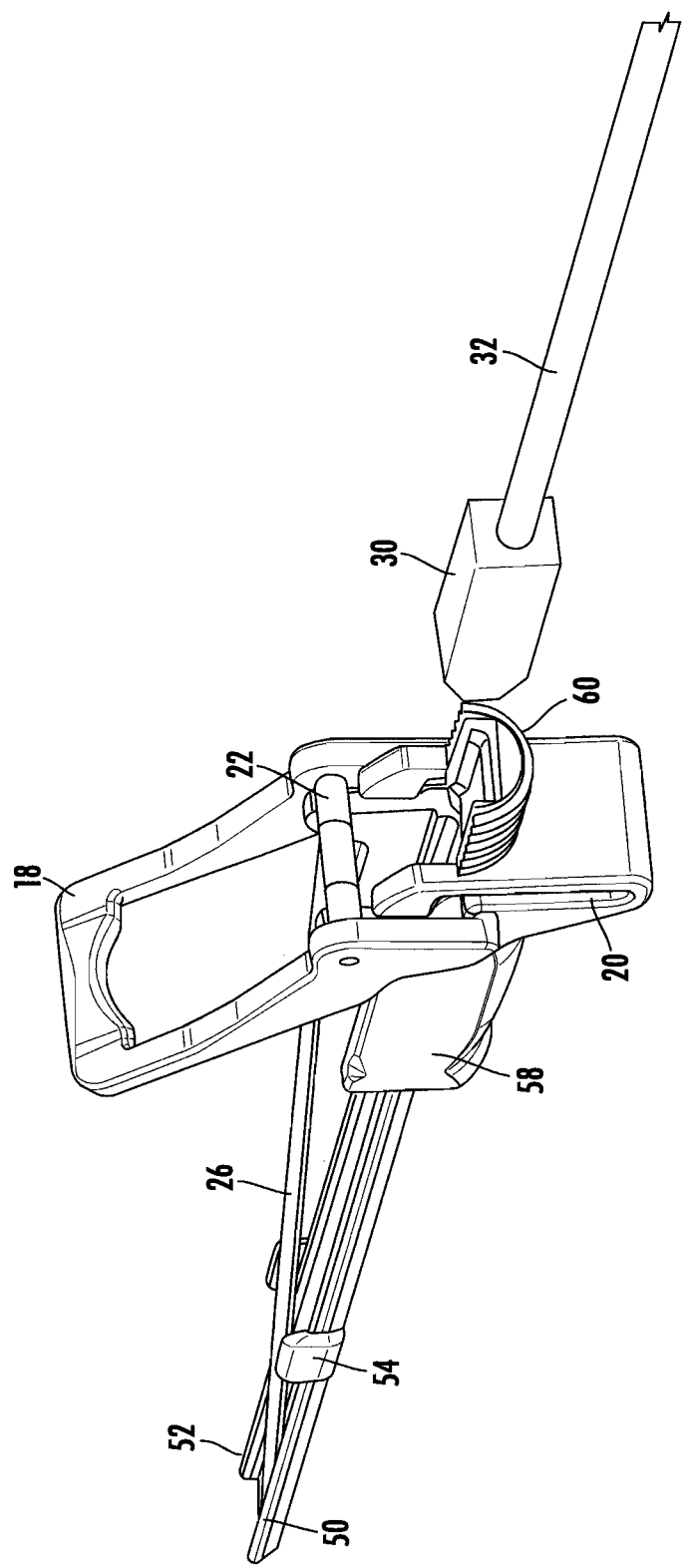
FIG. 14 is a top front left perspective view of the embodiment shown in FIG. 1 illustrating the device ready for insertion.
Figure 15:
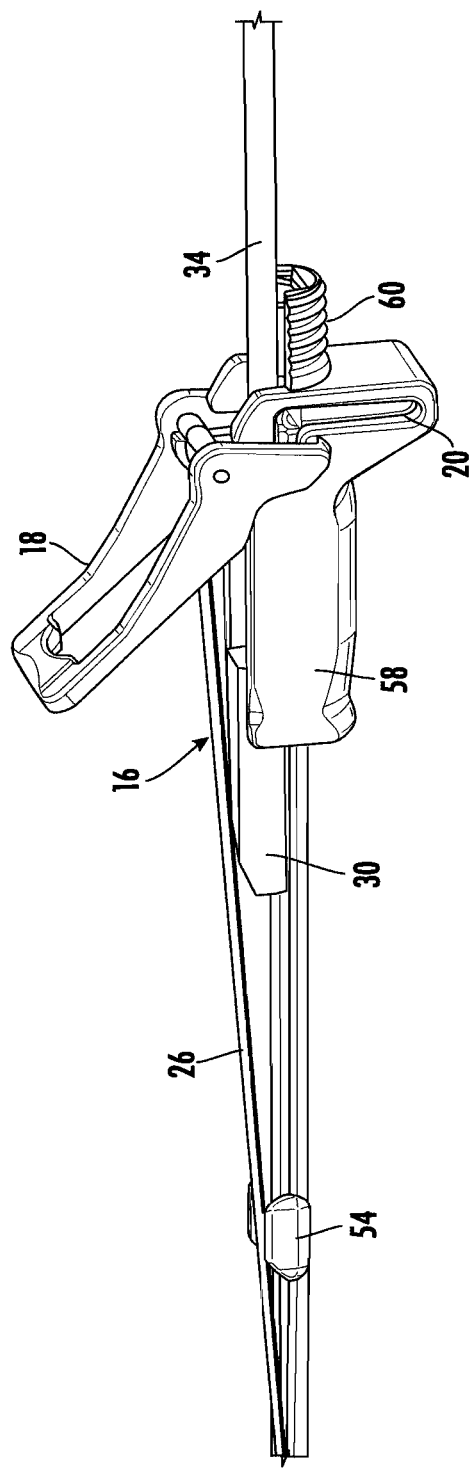
FIG. 15 is a rear perspective view illustrating an implant being traversed through the cannula.
Figure 16:
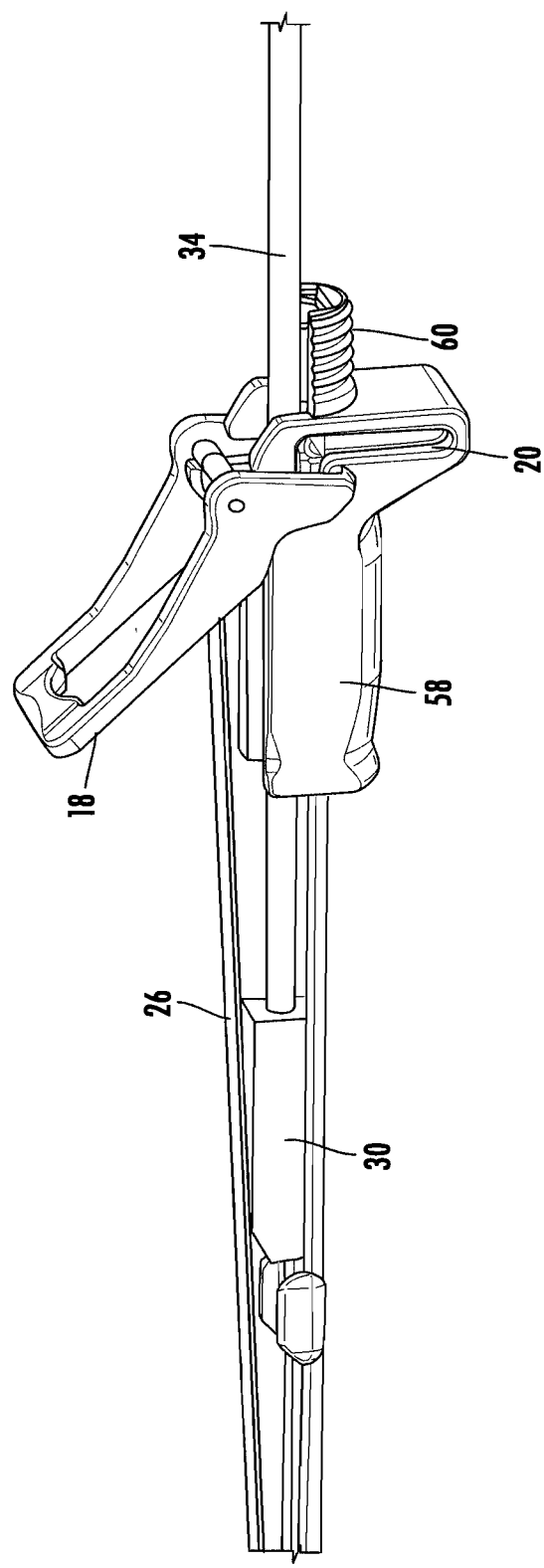
FIG. 16 is a rear perspective view illustrating an implant being traversed through the cannula.
Figure 17:
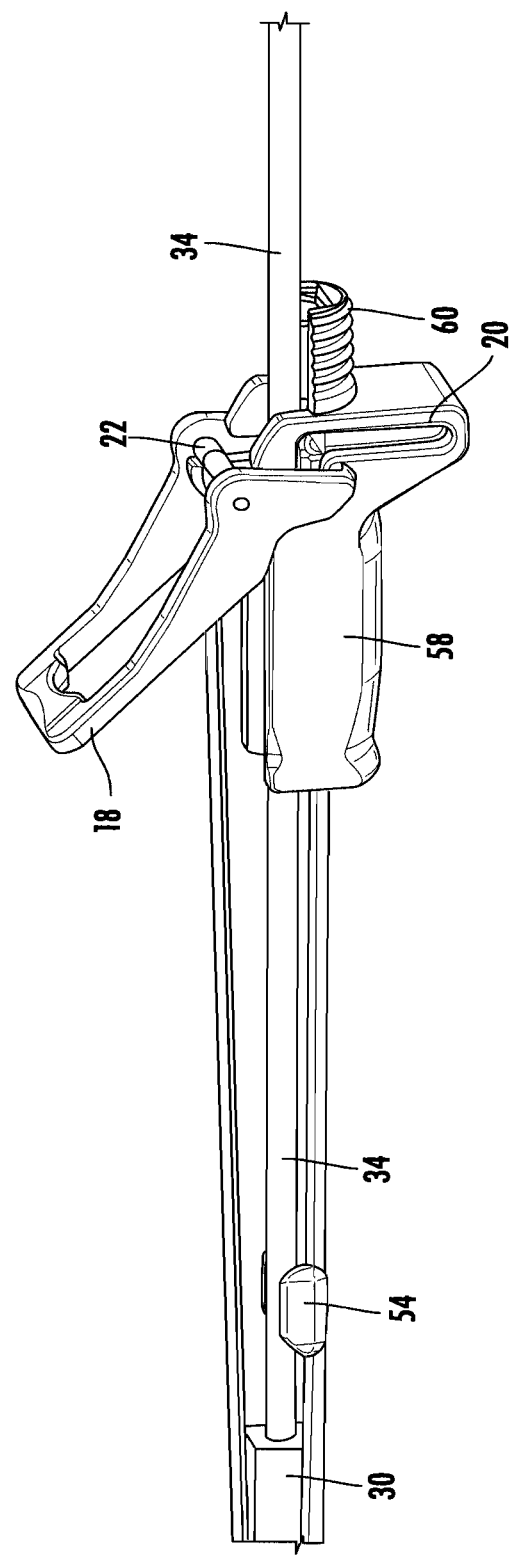
FIG. 17 is a rear perspective view illustrating an implant being traversed through the cannula.
Figure 18:
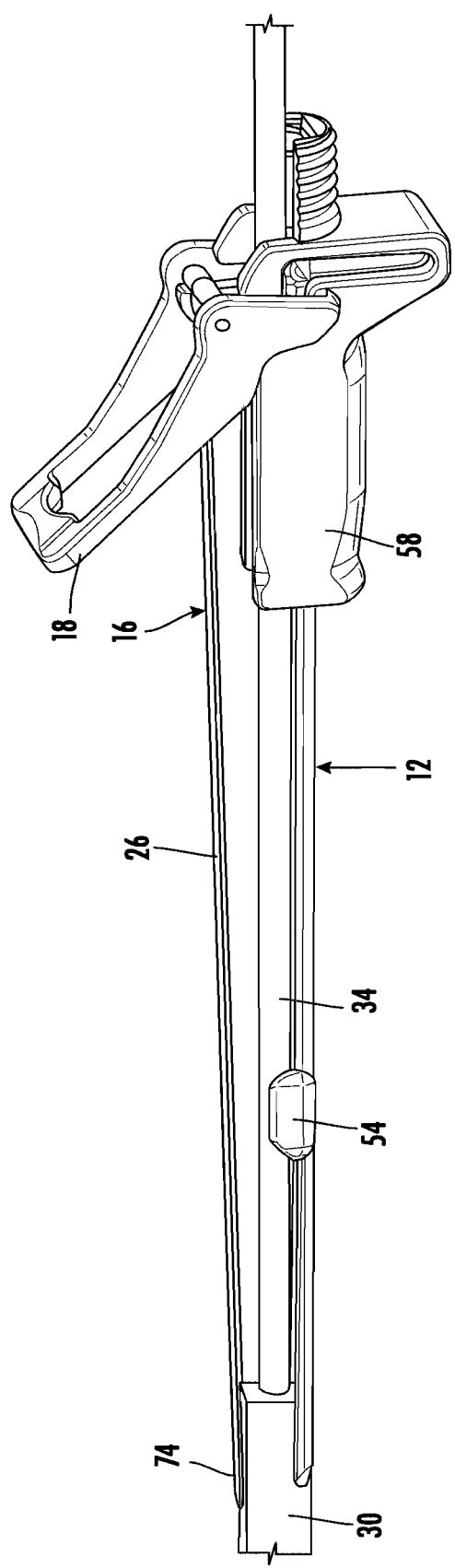
FIG. 18 is a rear perspective view illustrating an implant being traversed through the distal end of the cannula.
Figure 19:
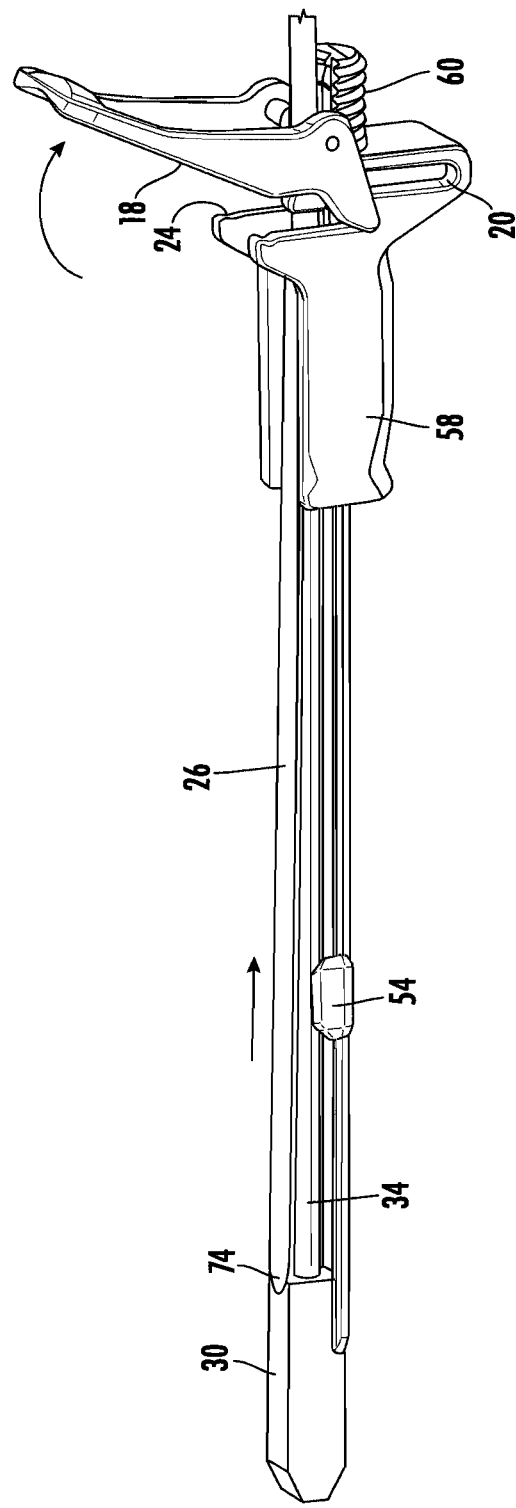
FIG. 19 is a rear perspective view illustrating removal of the expansion member with the lever.
Figure 20:
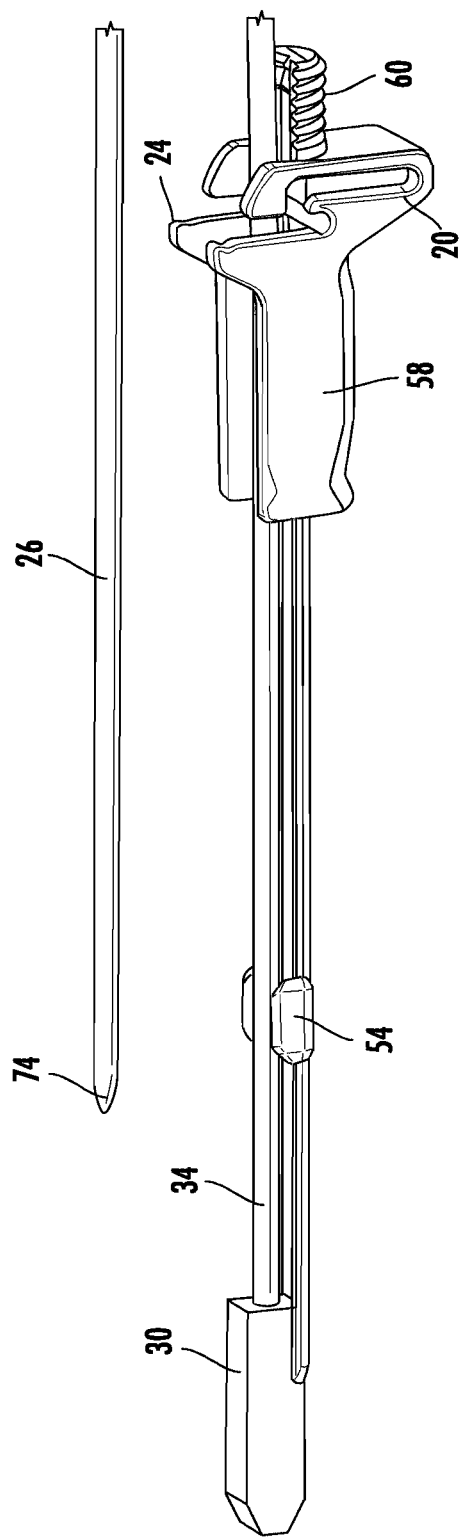
FIG. 20 is a rear perspective view illustrating the expansion member removed from the cannula.
Figure 21:
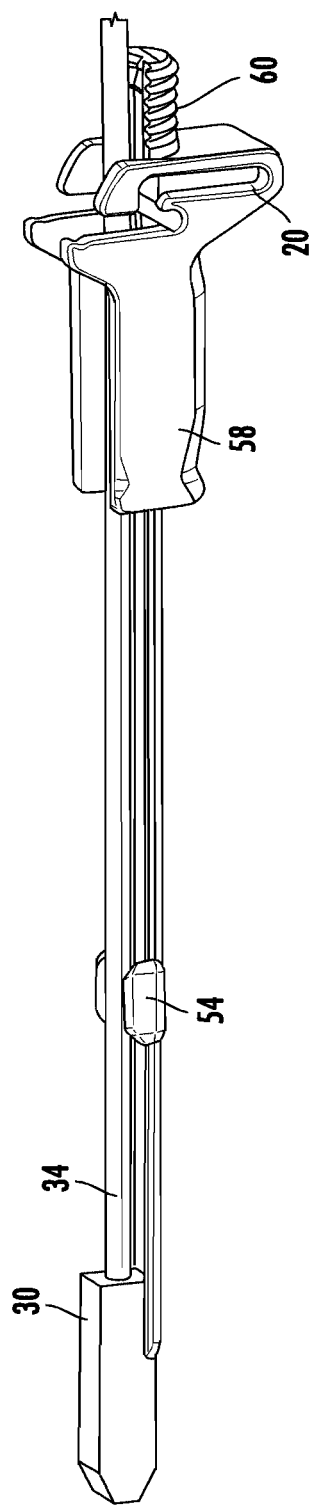
FIG. 21 is a rear perspective view illustrating the expansion member removed from the cannula.
Figure 22:
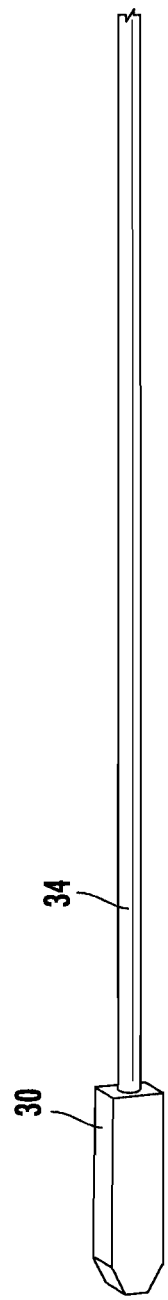
FIG. 22 is a perspective view of the implant in cooperation with a pusher member.

Referring generally to FIGS. 1-22, a cannula 10 for providing a dynamically expanding pathway for the insertion of a spinal implant is illustrated. The cannula 10 includes a slide assembly 12, a backing assembly 14, and an expansion assembly 16. In general, the cannula 10 is constructed and arranged for insertion of an implant 30 into a disc space. More particularly, the cannula 10 is constructed and arranged to insert an implant 30 into the disc space through the portion of the spine referred to as Kambin's triangle. However, the cannula 10 may be utilized for alternative insertion methods, including lateral, posterior and anterior, without departing from the scope of the invention. The cannula 10 is inserted as a hard-sided, compacted assembly as shown in FIGS. 1-4. The term hard-sided or rigid herein means that the device is sufficiently rigid to be inserted to the surgical site without flexing more than a few degrees from the longitudinal centerline of the assembly. In a most preferred embodiment, the device is sufficiently rigid to flex no more than 5 degrees from the longitudinal centerline or no more than 3 degrees from the longitudinal centerline or no more than 1 degree from the longitudinal centerline without departing from the scope of the invention. The cannula 10 may be inserted over a guide wire 34 or Kirshner wire. Alternatively, the cannula 10 may be inserted freehand without a guide wire without departing from the scope of the invention. After insertion, the backing assembly 14 and guide wire 34 are removed, leaving the slide assembly 12 and the expansion assembly 16. See FIGS. 7-9. Lever 18 is then repositioned from the closed position in control slot 20 (FIG. 10) to an open position (FIG. 11) where pivot pin 22 is supported in the open position catch 24. The open position separates the expansion member 26 and the slide assembly 12 at the rear end 28 portion of the cannula 10 for insertion of an implant 30. The implant 30 is positioned at the distal end of an implant inserter 32. The implant inserter 32 preferably includes a length that is longer than the cannula 10 so the implant 30 can be pushed through the cannula 10 and into a disc space (not shown). After the implant 30 is inserted into the disc space, the expansion member 26 may be removed from the slide assembly 12 by rotation of lever 18 about pivot pin 22 until control pin 42 contacts surface 36. Once the expansion member 26 has been withdrawn this distance, the lever 18 can be manipulated to thread pivot pin 22 through slot 38, allowing the lever to be utilized to pull the expansion member 26 along the slide surface 40 within the first side surface 50 and the second side surface 52 to remove the expansion member 26 from the slide assembly 12 while protecting the patient from the movement of the expansion member 26. The slide assembly 12 may be removed from the spine by pulling the slide assembly 12 by hand for completion of the surgical procedure. It should be noted that while the cannula 10 is described as being used for insertion of an implant, the cannula 10 may also be utilized for insertion of bone fragments, bone growth proteins, bone cement and the like without departing from the scope of the invention.

Referring to FIGS. 1-6 and 10-11, the cannula 10 is illustrated in a pre-insertion configuration. The pre-insertion configuration includes the slide assembly 12 and the backing assembly 14 secured together to enclose the expansion member 26. The slide assembly 12 is preferably constructed from a rigid material, such as stainless steel or titanium, to have rigidity as described above. However, sufficiently rigid polymeric materials such as carbon fiber, fiber strengthened plastics or plastics having a low modulus of elasticity or other biocompatible metals may be utilized without departing from the scope of the invention. The slide assembly first end 44 is generally U-shaped having a tapered distal surface 48, a first side surface 50 and a second side surface 52. The first and second side surfaces 50, 52, respectively, each preferably include a catch 54 including a slot 56 for receiving a portion of the backing assembly 14 to interlock the respective first ends pf the slide assembly 12 and the backing assembly 14 together for insertion of the cannula 10. In addition to providing a holding area for the expansion member 26 during insertion, the first and second side surfaces 50, 52 provide a guide way for the implant 30 when the cannula is opened. The second end 46 of the slide assembly 12 preferably includes the operational control block 58 for the cannula. The control block 58 includes the control slot 20 constructed and arranged to cooperate with lever 18 and pivot pin 22, as well as control pin 42 to control opening, closing and removal of the expansion member 26. The control slot 20 is contoured and includes the open position catch 24. By utilization of the contours and catches, the expansion member 26 can be positioned against the slide surface 40 for insertion into a patient, the rear portion opened by placing the pivot pin 22 in the open position catch 24 (FIG. 11) for insertion of an implant 30, and for rotation of the lever 18 to remove the expansion member 26 from the cannula 10. The outer surfaces 36 of the slide assembly 12 are also contoured to limit the movement of the lever 18. The lever 18 can thereby be rotated until the lever contacts surface 36. The second end 46 of the slide assembly 12 also includes a thread portion 60 for cooperation with thumb screw 62. The thumb screw 62 is secured to the backing assembly second end 66 for free rotation about a longitudinal centerline of the backing assembly 14. In operation, the backing assembly 14 is slid between the first and second side surfaces 44, 46 until keys 68 (FIG. 9) engage the catch slot 56, locking the first ends of the slide assembly 12 and the backing assembly 14 together. The thumb screw 62 can then be rotated to engage the internal threads 70 (FIG. 7) with the thread portion 60 of the slide assembly 12. Disengagement of the backing assembly 14 from the slide assembly 12 requires the thumb screw 62 to be rotated to disengage the internal threads 70 from the thread portion 60, pulling the backing assembly 14 rearwardly with respect to the slide assembly 12, and allowing the backing assembly 14 to be fully removed by hand. It should be noted that the rearward motion of the backing assembly 14 that is provided by the thumb screw 62 is preferably suitable for retraction of the backing assembly 14 from the disc space. Anvil 72 is also provided on the distal second end 46 of the backing assembly 14 for impaction with a mallet or the like when needed to insert the front end portion 27 of the cannula 10 into a disc space.

Referring generally to the Figs., and more particularly to FIGS. 11-22, the expansion member 26 of the expansion assembly 16 is illustrated. In general, the expansion member 26 is constructed from a metal material having a temper and hardness sufficient to dynamically open a pathway through the tissue of the patient as an implant 30 is traversed along the slide assembly 12 and returning to a closed position after passage of the implant 30. In this manner, trauma to the tissue and nerves of the patient are reduced. In a most preferred embodiment, the expansion member 26 is constructed from a Nitinol material having a spring temper. However, any metal or polymer material suitable for sliding along an outer surface of the implant 30 and displacing the tissue without permanent deformation of the expansion member 26 may be utilized without departing from the scope of the invention. In a most preferred embodiment, the expansion member 26 is about 0.02 inches in thickness, having an expansion member first end 74 and an expansion member second end 76. The first end 74 of the expansion member may be tapered both in thickness and in width. The outer edges are preferably rounded to reduce the possibility of cutting tissue. The second end 76 of the expansion member 26 is connected to the control pin 42. In a most preferred embodiment, the expansion member 26 is rolled around the control pin 42 so that the lever 18 can be rotated without rotation of the second end 76 of the expansion member 26. In this manner, the lever 18 can be rotated from the expansion member open position to retract the expansion member from the disc space as needed. For retraction of the expansion member 26, the control pins 42 are positioned in the open position catches 24 in control slot 20. This position opens the cannula 10 for insertion of an implant 30 and prevents forward movement of the expansion member 26 by preventing forward rotation of the lever 18. The lever 18 can be rotated until the lever 18 contacts surface 36; at which point the pivot pins 22 can be removed from the control slot 20 and the expansion member 26 can be pulled outwardly so that the expansion member 26 follows the slide assembly 12 until removed.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A dynamically expanding cannula for insertion of a spinal implant comprising:
    a slide assembly for providing a guide way for an implant, the slide assembly including a control block, the control block constructed and arranged for securing a backing assembly to the slide assembly;
    said backing assembly removably secured to the slide assembly; and
    a flexible expansion assembly including a flexible expansion member that is adapted to expand in an area around the implant as the implant is progressed through the dynamically expanding cannula from a first end of the dynamically expanding cannula to a second end of the dynamically expanding cannula and retract to a smaller profile after the implant passes, the control block including a control slot, a lever, a pivot pin and a control pin extending across said lever and positioned to follow the contours of the control slot, the lever operational to position the pivot pin and the control pin within the contours of the control slot for controlling the expansion of the flexible expansion member, the flexible expansion assembly is positioned between the slide assembly and the backing assembly for insertion into a surgical site.

2. The dynamically expanding cannula of claim 1 wherein said slide assembly and said backing assembly are sized and shaped for insertion into a disc space in a spine of a human.

3. The dynamically expanding cannula claim 2 wherein said slide assembly and said backing assembly are sized and shaped for insertion into the disc space through a Kambin's triangle portion of the spine of a human.

4. The dynamically expanding cannula of claim 2 wherein the slide assembly includes a first end that is generally U-shaped having a tapered distal surface, a first side surface and a second side surface, a portion of the flexible expansion assembly is sized to fit between the first side surface and the second side surface, the slide assembly and the backing assembly constructed and arranged to be secured together so that a portion of the backing assembly is also positioned between the first side surface and the second side surface wherein the dynamically expanding cannula is inserted as a hard-sided assembly.

5. The dynamically expanding cannula of claim 4 wherein the dynamically expanding cannula includes a guide wire port extending through the backing assembly wherein the dynamically expanding cannula can be passed over a guide wire to a surgical site.

6. The dynamically expanding cannula of claim 4 wherein the first and second side surfaces each include a catch, the catch including a slot for receiving the portion of the backing assembly to interlock the respective first end of the slide assembly and the backing assembly together for insertion of the dynamically expanding cannula.

7. The dynamically expanding cannula of claim 6 wherein the backing assembly is removable after insertion of the dynamically expanding cannula to the surgical site, leaving the slide assembly and the flexible expansion assembly in place in a compact arrangement.

8. The dynamically expanding cannula of claim 7 wherein the control block includes a threaded portion for cooperation with a thumb screw for securing the backing assembly to the slide assembly.

9. The dynamically expanding cannula of claim 8 wherein the thumb screw is secured to said backing assembly for free rotation about a longitudinal centerline of the backing assembly while still being secured thereto and said threaded portion is a threaded portion of a cylinder having a U-shape along an inner surface thereof, causing the backing assembly to move linearly along said U-shaped inner surface until the threaded thumb screw is clear of the threads.

10. The dynamically expanding cannula of claim 1 wherein the control slot is contoured and includes a closed position for insertion into a patient, an open position catch for insertion of the implant into the dynamically expanding cannula and by rotation of the lever, the expansion member can be removed from the slide assembly.

11. The dynamically expanding cannula of claim 1 wherein the expansion member is constructed from a metal material having a temper and hardness sufficient to dynamically open a pathway through the tissue of the patient as the implant is traversed along the slide assembly, returning to a closed position after passage of the implant.

12. The dynamically expanding cannula of claim 11 wherein the expansion member is constructed from a nitinol material having a spring temper.

13. The dynamically expanding cannula of claim 12 wherein the expansion member is about 0.02 inches in thickness, having an expansion member first end and an expansion member second end, the first end of the expansion member is tapered both in thickness and in width.

14. A dynamically expanding cannula for insertion of a spinal implant comprising:
   a slide assembly for providing a guide way for an implant, the slide assembly including a control block, the control block constructed and arranged for securing a backing assembly to the slide assembly, the control block including a control slot, a lever, a pivot pin and a control pin extending across said lever and positioned to follow the contours of the control slot, the lever operational to position the pivot pin and the control pin within the contours of the control slot for controlling the expansion of a flexible expansion member;
   a backing assembly removably secured to the slide assembly; and
   a flexible expansion assembly including said flexible expansion member that is adapted to expand in an area around the implant as the implant is progressed through the dynamically expanding cannula from a first end of the dynamically expanding cannula to a second end of the dynamically expanding cannula wherein the flexible expansion member is constructed from a metal material having a temper and hardness sufficient to dynamically open a pathway through the tissue of the patient as an implant is traversed along the slide assembly, returning to a smaller profile after passage of the implant, the flexible expansion assembly positioned between the slide assembly and the backing assembly for insertion into a surgical site.

15. The dynamically expanding cannula of claim 14 wherein the slide assembly and the backing assembly are secured together enclosing the flexible expansion member for insertion into the surgical site.

16. The dynamically expanding cannula of claim 15 wherein the slide assembly and the backing assembly are rigid.

17. The dynamically expanding cannula of claim 16 wherein the backing assembly is removable from the slide assembly after insertion of the dynamically expanding cannula system.

* * * * *